United States Patent
Nishimura et al.

(10) Patent No.: US 9,310,358 B2
(45) Date of Patent: Apr. 12, 2016

(54) SUGAR CHAIN ARRAY

(75) Inventors: Shin-Ichiro Nishimura, Sapporo (JP); Takahiko Matsushita, Sapporo (JP); Hideyuki Shimaoka, Tokyo (JP); Wataru Takada, Tokyo (JP); Kohta Igarashi, Tokyo (JP); Midori Abe, Tokyo (JP); Hiroki Abe, Tokyo (JP); Masao Fukushima, Tokyo (JP)

(73) Assignees: SUMITOMO BAKELITE CO., LTD., Tokyo (JP); NATIONAL UNIVERSITY CORPORATION HOKKAIDO UNIVERSITY, Sapporo-shi (JP)

( * ) Notice: Subject to any disclaimer, the term of this patent is extended or adjusted under 35 U.S.C. 154(b) by 301 days.

(21) Appl. No.: 13/812,787

(22) PCT Filed: Jul. 29, 2011

(86) PCT No.: PCT/JP2011/067433
§ 371 (c)(1),
(2), (4) Date: Apr. 5, 2013

(87) PCT Pub. No.: WO2012/015029
PCT Pub. Date: Feb. 2, 2012

(65) Prior Publication Data
US 2013/0196881 A1 Aug. 1, 2013

(30) Foreign Application Priority Data
Jul. 30, 2010 (JP) .................................. 2010-171561

(51) Int. Cl.
*G01N 33/53* (2006.01)
*G01N 33/543* (2006.01)
*G01N 33/66* (2006.01)

(52) U.S. Cl.
CPC ...... *G01N 33/5308* (2013.01); *G01N 33/54393* (2013.01); *G01N 33/66* (2013.01)

(58) Field of Classification Search
None
See application file for complete search history.

(56) References Cited

U.S. PATENT DOCUMENTS

2004/0258927 A1* 12/2004 Conzone et al. .............. 428/429
2004/0259142 A1* 12/2004 Chai et al. .......................... 435/6
2006/0252030 A1 11/2006 In-Jae et al.

FOREIGN PATENT DOCUMENTS

| EP | 1 577 293 A1 | 9/2005 |
|---|---|---|
| JP | 2004 115616 | 4/2004 |
| JP | 2006 78418 | 3/2006 |
| JP | 2007-326920 A | 12/2007 |
| JP | 2008-541011 A | 11/2008 |
| JP | 2008 304427 | 12/2008 |
| WO | WO 2005/097844 A1 | 10/2005 |
| WO | WO 2006/121230 A1 | 11/2006 |
| WO | WO 2009/057755 A1 | 5/2009 |

OTHER PUBLICATIONS

Takada et al., JP 2008-304427 A, Dec. 2008, machine translation. Retreived on Jan. 28, 2015 from http://dossier1.ipdl.inpit.go.jp/AIPN/odse_top_dn.ipdl?N0000=7400.*
Igarashi, K., et al., "Development and Application of Glycan Chip & Microarray," BIO Industry, vol. 26, No. 7, pp. 63-70, (Jul. 12, 2009).
International Search Report Issued Oct. 11, 2011 in PCT/JP11/67433 Filed Jul. 29, 2011.
Extended European Search Report issued Jan. 23, 2015 in Patent Application No. 11812618.4.
Myung-ryul Lee et al., "Facile Preparation of Carbohydrate Microarrays by Site-Specific, Covalent Immobilization of Unmodified Carbohydrates on Hydrazide-Coated Glass Slides", Organic Letters, vol. 7, No. 19, XP009135016, Sep. 15, 2005, pp. 4269-4272.
Sungjin Park et al., "Construction of Carbohydrate Microarrays by Using One-Step, Direct Immobilizations of Diverse Unmodified Glycans on Solid Surfaces", Bioconjugate Chem., vol. 20, No. 1, XP055162171, Jan. 21, 2009, pp. 155-162.
Japanese Office Action dated Jan. 27, 2016, in Japanese Patent Application No. 2015-031370 with English Translation (6 pages).

* cited by examiner

*Primary Examiner* — Eric Olson
*Assistant Examiner* — Dale R Miller
(74) *Attorney, Agent, or Firm* — Oblon, McClelland, Maier & Neustadt, L.L.P.

(57) ABSTRACT

A sugar chain array containing a sugar chain immobilized thereon for detecting binding between an analyte and a sugar chain, and a sugar chain array having the sugar chain immobilized thereon that is capable of inhibiting non-specific adsorption and binding of an analyte without having to coat the array with an adsorption inhibitor. A specific sugar chain is immobilized on the array, and is useful for detecting binding between the sugar chain and an analyte, such as a pathogen of an infectious disease or an excretion thereof. In addition, in the array, when a base material is coated with a polymeric compound having a unit having a primary amino group, a unit for maintaining hydrophilicity, and a unit having a hydrophobic group, the sugar chain is immobilized efficiently and non-specific adsorption and binding of the analyte can be effectively inhibited.

13 Claims, No Drawings

SUGAR CHAIN ARRAY

TECHNICAL FIELD

The present invention relates to a sugar chain array capable of detecting binding between an analyte and a sugar chain.

BACKGROUND ART

In the field of biochemistry, sugar chains have attracted attention in recent years as a third type of chain following nucleic acids and proteins. In particular, research has been conducted on their involvement with cell differentiation and malignant transformation, immune response and fertilization, and attempts are continuing towards the development of new pharmaceuticals and medical materials.

In addition, sugar chains serve as receptors for numerous toxins, viruses and bacteria and are also attracting attention as tumor markers, and attempts are similarly continuing towards the development of new pharmaceuticals and medical materials in these fields as well.

However, although the importance of research on sugar chains is recognized, due to their complex structure and diversity, the pace at which this research has progressed is considerably slower in comparison with the first and second types of chains in the form of nucleic acids and proteins.

The objective of proceeding with this research is to develop various methods for purifying sugar chains. In addition, since numerous cases of sugar chains functioning as ligands for cell receptors have been confirmed rather than these sugar chains functioning independently, development has also proceeded on base materials for immobilizing various sugar chains to enable them to be used in analyzing sugar chain receptors (Patent Document 1, Patent Document 2).

Patent Document 1 indicates a method for producing a sugar chain array in which a sugar chain is bound to a first functional group, and a third functional group is bound to a chromophore by using a second functional group as a solid support. It is described in the examples thereof that a blocking procedure is carried out using bovine serum albumin in order to prevent non-specific adsorption following sugar chain immobilization. However, carrying out this blocking procedure following sugar chain immobilization is both complicated and troublesome.

On the other hand, Patent Document 2 describes a method for immobilizing a sugar chain on a base material through a spacer, and indicates that non-specific adsorption is inhibited by using a hydrophilic compound for the spacer. However, in this method, it is necessary to introduce an acetyl halide group into the solid support when immobilizing the sugar chain on the base material, and although this is comparatively easy in the case the material of the base material is glass, this method lacks versatility with respect to other materials.

In this manner, in addition to delays in the development of suitable techniques and base materials for immobilizing sugar chains, development has also been delayed with respect to sugar chain arrays on which sugar chains are immobilized that are useful for analyzing interactions between analytes and sugar chains.

PRIOR ART DOCUMENTS

Patent Documents

[Patent Document 1] Japanese Unexamined Patent Application, First Publication No. 2004-115616
[Patent Document 2] Japanese Unexamined Patent Application, First Publication No. 2006-078418

DISCLOSURE OF THE INVENTION

Problems to be Solved by the Invention

With the foregoing in view, an object of the present invention is to provide a sugar chain array having a sugar chain immobilized thereon that is useful for detecting binding between an analyte and a sugar chain. Another object of the present invention is to provide a sugar chain array having the aforementioned sugar chain immobilized thereon that is capable of inhibiting non-specific adsorption and binding of an analyte without having to coat the sugar chain array with an adsorption inhibitor.

Means for Solving the Problems

As a result of conducting extensive studies to achieve the aforementioned objects, the inventors of the present invention found that a sugar chain array having the sugar chains described in the following Tables 1 to 6 immobilized thereon is useful for detecting interaction between the sugar chains and analytes such as pathogens of infectious diseases and secretions thereof. Moreover, the inventors of the present invention found that, when a base material coated with a polymeric compound comprising a unit having a primary amine group, a unit for maintaining hydrophilicity, and a unit having a hydrophobic group is used in this sugar chain array, the sugar chain is immobilized efficiently and non-specific adsorption and binding of the analyte can be effectively inhibited, thereby leading to completion of the present invention.

More specifically, the present invention provides the inventions indicated below.

[1] A sugar chain array comprising a base material and at least one sugar chain selected from the group consisting of sugar chains described in the following Tables 1 to 6:

TABLE 1

| | | |
|---|---|---|
| 1 | Glc | Acyl1-O-6Glc |
| 2 | Galβ1-4Glc | Xyl |
| 3 | Gal | Galα1-4Gal |
| 4 | GalNAcα1-3GalNAcβ1-3Galα1-4Gal | Galα1-4Galβ1-4Glc |
| 5 | Galα1-3Galα1-4Galβ1-4Glc | Galα1-3Galα1-3Galα1-4Galβ1-4Glc |
| 6 | Galα1-3Galα1-3Galα1-3Galα1-4Galβ1-4Glc | GalNAcβ1-3Galα1-4Galβ1-4Glc |
| 7 | GalNAcα1-3GalNAcβ1-3Galα1-3Galβ1-4Glc | Galβ1-3GalNAcβ1-3Galα1-4Galβ1-4Glc |
| 8 | GalNAcβ1-3Galα1-3Galα1-4Glc | GalNAcβ1-3Galα1-3Galα1-3Galα1-4Glc |
| 9 | GalNAcβ1-3Galα1-3Galα1-3Galα1-3Galα1-4Galβ1-4Glc | Galα1-3Galβ1-4Glc |
| 10 | GalNAcβ1-3Galα1-3Galβ1-4Glc | GlcNAcβ1-3Galβ1-4Glc |
| 11 | Galβ1-3GlcNAcβ1-3Galβ1-4Glc | Galβ1-4GlcNAcβ1-3Galβ1-4Glc |
| 12 | Galα1-3Galβ1-4GlcNAcβ1-3Galβ1-4Glc | Galβ1-3Galβ1-4GlcNAcβ1-3Galβ1-4Glc |

TABLE 1-continued

| | | |
|---|---|---|
| 13 | Galα1-4Galβ1-4GlcNAcβ1-3Galβ1-4Glc | Galβ1-4GlcNAcβ1-3Galβ1-4GlcNAcβ1-3Galβ1-4Glc |
| 14 | GalNAcβ1-3Galβ1-4GlcNAcβ1-3Galβ1-4Glc | Galα1-3Galβ1-4GlcNAcβ1-3Galβ1-4GlcNAcβ1-3Galβ1-4Glc |
| 15 | Galβ1-4GlcNAcβ1-3(Galβ1-4GlcNAcβ1-6)Galα1-4GlcNAcβ1-3Galβ1-4Glc | GalNAcα1-3Galβ1-4GlcNAcβ1-3(Galβ1-4GlcNAcβ1-6)Galβ1-4GlcNAcβ1-3Galβ1-4Glc |
| 16 | Galα1-3Galβ1-4GlcNAcβ1-3(Galα1-3Galβ1-4GlcNAcβ1-6)Galα1-4GlcNAcβ1-3Galβ1-4Glc | Galα1-3Galβ1-4GlcNAcβ1-3(Galα1-3Galβ1-4GlcNAcβ1-6)Galβ1-4GlcNAcβ1-3(Galα1-3Galβ1-4GlcNAcβ1-6)Galβ1-4GlcNAcβ1-3Galβ1-4Glc |
| 17 | GalNAcβ1-4Galβ1-4Glc | Galβ1-3GalNAcβ1-4Galβ1-4Glc |
| 18 | GlcNAcβ1-3(GalNAcβ1-4)Galβ1-4Glc | Galα1-3Galβ1-4GlcNAcβ1-3(GalNAcβ1-4)Galβ1-4Glc |
| 19 | HSO3-3Glc | HSO3-3Galβ1-4Glc |
| 20 | HSO3-3Gal | HSO3-3GalNAcβ1-3Galα1-4Galβ1-4Glc |
| 21 | HSO3-3Galβ1-3GaNAcβ1-3Galα1-4Galβ1-4Glc | GalNAcβ1-4(HSO3-3)Galβ1-4Glc |
| 22 | HSO3-3GalNAcβ1-4(HSO3-3)Galβ1-4Gal | Galβ1-3GalNAcβ1-4(HSO3-3)Galβ1-4Glc |
| 23 | HSO3-3Galβ1-3GalNAcβ1-4Galβ1-4Glc | HSO3-3Galβ1-3GalNAcβ1-4(HSO3-3)Galβ1-4Glc |
| 24 | HSO3-6GlcNAcβ1-3Galβ1-4Glc | Galβ1-4(HSO3-6)GlcNAcβ1-3Galβ1-4Glc |
| 25 | HSO3-3GlcUAβ1-3Galβ1-4GlcNAcβ1-3Galβ1-4Glc | HSO3-3GlcUAβ1-3(Galβ1-4GlcNAcβ1)$_2$-3Galβ1-4Glc |
| 26 | HSO3-3Gal1-4Gal1-4Glc | Fuc |

TABLE 2

| | | |
|---|---|---|
| 27 | Fucα1-2Galβ1-4Glc | GalNAcα1-3(Fucα1-2)Galβ1-4Glc |
| 28 | Fucα1-2Galα1-3Galα1-4Galβ1-4Glc | Fucα1-2Galβ1-3GalNAcβ1-3Galα1-4Galβ1-4Glc |
| 29 | Galβ1-4(Fucα1-3)GlcNAcβ1-6(Galβ1-3)GalNAcβ1-3Galα1-4Galβ1-4Glc | Fucα1-2Galα1-3Galβ1-4Glc |
| 30 | Galα1-3(Fucα1-2)Galβ1-4Glc | Galα1-3(Fucα1-2)Galβ1-3GalNAcβ1-3Galα1-3Galβ1-4Glc |
| 31 | Fucα1-2Galβ1-3GalNAcβ1-4Galβ1-4Glc | Galα1-3Galβ1-3GalNAcβ1-4Galβ1-4Glic |
| 32 | Galα1-3(Fucα1-2)Galβ1-3GalNAcβ1-3Galβ1-4Glc | Fucα1-2Galβ1-3Glcp1-3Galβ1-4Glc |
| 33 | Galβ1-3(Fucα1-4)GlcNAcβ1-3Galβ1-4Glc | Galα1-3(Fucα1-2)Galβ1-3GlcNAcβ1-3Galβ1-4Glc |
| 34 | GalNAcα1-3(Fucα1-2)Galβ1-3GlcNAcβ1-3Galβ1-4Glc | Fucα1-2Galβ1-3(Fucα1-4)GlcNAcβ1-3Galβ1-4Glc |
| 35 | Galα1-3(Fucα1-2)Galβ1-3(Fucα1-4)GlcNAcβ1-3Galβ1-4Glc | GalNAcα1-3(Fucα1-2)Galβ1-3(Fucα1-4)GlcNAcβ1-3Galβ1-4Glc |
| 36 | Fucβ1-2Galβ1-4GlcNAcβ1-3Galβ1-3GlcNAcβ1-3Galβ1-4Glc | Galβ1-3(Fucα1-4)GlcNAcβ1-3Galβ1-3GlcNAcβ1-3Galβ1-4Glc |
| 37 | Fucα1-2Galβ1-4(Fucα1-3)GlcNAcβ1-3Galβ1-3GlcNAcβ1-3Galβ1-4Glc | Fucα1-2Galβ1-4(Fucα1-3)GlcNAcβ1-3(Fucα1-4)GlcNAcβ1-3Galβ1-4Glc |
| 38 | Fucα1-2Galβ1-3GlcNAcβ1-3(Fucα1-2Galβ1-3(4)GlcNAcβ1-6)Galβ1-3GlcNAcβ1-3Galβ1-4Glc | GalNAcα1-3(Fucα1-2)Galβ1-3GlcNAcβ1-3(GalNAcα1-3(Fucα1-4)Galβ1-3GlcNAcβ1-6)Galβ1-3GlcNAcβ1-3Galβ1-4Glc |
| 39 | GalNAcα1-3(Fucα1-2)Galβ1-3GlcNAcβ1-3(GalNAcα1-3(Fucα1-2)Galβ1-4GlcNAcβ1-6)Galβ1-3GlcNAcβ1-3Galβ1-4Glc | Fucα1-2Galβ1-4GlcNAcβ1-3Galβ1-4Glc |
| 40 | Galβ1-4(Fucα1-3)GlcNAcβ1-3Galβ1-4Glc | Galα1-3(Fucα1-2)Galβ1-4GlcNAcβ1-3Galβ1-4Glc |
| 41 | GalNAcα1-3(Fucα1-2)Galβ1-4GlcNAcβ1-3Galβ1-4Glc | Fucα1-2Galβ1-4(Fucα1-3)GlcNAcβ1-3Galβ1-4Glc |
| 42 | Fucα1-2Galβ1-4GlcNAcβ1-3Galβ1-4GlcNAcβ1-3Galβ1-4Glc | GalNAcα1-3(Fucα1-2)Galβ1-4(Fucα1-3)GlcNAcβ1-3Galβ1-4Glc |
| 43 | Galα1-3(Fucα1-2)Galβ1-4GlcNAcβ1-3Galβ1-4GlcNAcβ1-3Galβ1-4Glc | GalNAcα1-3(Fucα1-2)Galβ1-4GlcNAcβ1-3Galβ1-4GlcNAcβ1-3Galβ1-4Glc |
| 44 | Galβ1-4(Fucα1-3)GlcNAcβ1-3Galβ1-4(Fucα1-3)GlcNAcβ1-3Galβ1-4Glc | Fucα1-2Galβ1-4(Fucα1-3)GlcNAcβ1-3Galβ1-4GlcNAcβ1-3Galβ1-4Glc |
| 45 | Fucα1-2Galβ1-4(Fucα1-3)GlcNAcβ1-3Galβ1-4GlcNAcβ1-3Galβ1-4Glc | Fucα1-2Galβ1-4(Fucα1-3)GlcNAcβ1-3Galβ1-4(Fucα1-3)GlcNAcβ1-3Galβ1-4Glc |
| 46 | Galβ1-4(Fucα1-3)GlcNAcβ1-3Galβ1-4GlcNAcβ1-3Galβ1-4Glc | Galβ1-4GlcNAcβ1-3Galβ1-4(Fucα1-3)GlcNAcβ1-3Galβ1-4Glc |
| 47 | Galβ1-3GalNAcα1-3(Fucα1-2)Galβ1-4GlcNAcβ1-3Galβ1-4Glc | Galβ1-3(Fucα1-4)GlcNAcβ1-3Galβ1-4GlcNAcβ1-3Galβ1-4Glc |

TABLE 3

| | | |
|---|---|---|
| 48 | GalNAcα1-3(Fucα1-2)Galβ1-3GalNAcα1-3(Fucα1-2)Galβ1-4GlcNAcβ1-3Galβ1-4GlcNAcβ1-3Galβ1-4Glc | Galβ1-4(Fucα1-3)GlcNAcβ1-3Galβ1-4GlcNAcβ1-3Galβ1-4GlcNAcβ1-3Galβ1-4Glc |

TABLE 3-continued

| | | |
|---|---|---|
| 49 | Galβ1-4(Fucα1-3)GlcNAcβ1-3Galβ1-4(Fucα1-3)GlcNAcβ1-3Galβ1-4GlcNAcβ1-3Galβ1-4Glc | Galβ1-4(Fucα1-3)GlcNAcβ1-3Galβ1-4(Fucα1-3)GlcNAcβ1-3Galβ1-4(Fucα1-3)GlcNAcβ1-3Galβ1-4Glc |
| 50 | Galβ1-4GlcNAcβ1-3Galβ1-4(Fucα1-3)GlcNAcβ1-(3Galβ1-4GlcNAcβ1)2-3Galβ1-4Glc | Fucα1-2Galβ1-4GlcNAcβ1-3(Fucα1-2Galβ1-4GlcNAcβ1-6)Galβ1-4GlcNAcβ1-3Galβ1-4Glc |
| 51 | GalNAcα1-3(Fucα1-2)Galβ1-4GlcNAcβ1-3(GalNAcα1-3(Fucα1-2)Galβ1-4GlcNAcβ1-6)Galβ1-4GlcNAcβ1-3Galβ1-4Glc | Galα1-3(Fucα1-2)Galβ1-4GlcNAcβ1-3(Galα1-3(Fucα1-2)Galβ1-4GlcNAcβ1-6)Galβ1-4GlcNAcβ1-3Galβ1-4Glc |
| 52 | GalNAcα1-3(Fucα1-2)Galβ1-4GlcNAcβ1-3Galβ1-4GlcNAcβ1-3(GalNAcα1-3(Fucα1-2)Galβ1-4GlcNAcβ1-6)Galβ1-4GlcNAcβ1-3Galβ1-4Glc | Galα1-3(Fucα1-2)Galβ1-4GlcNAcβ1-3Galβ1-4GlcNAcβ1-3(Galα1-3(Fucα1-2)Galβ1-4GlcNAcβ1-6)Galβ1-4GlcNAcβ1-3Galβ1-4Glc |
| 53 | Galα1-3(Fucα1-2)Galβ1-4GlcNAcβ1-3(Galα1-3(Fucα1-2)Galβ1-4GlcNAcβ1-6)Galβ1-4GlcNAcβ1-3Galβ1-4GlcNAcβ1-3Galβ1-4Glc | Fucα1-3GalNAcβ1-3Galα1-3Galβ1-4GlcNAcβ1-3(GlcNAcβ1-4)Galβ1-4Glc |
| 54 | GalNAcα1-3(Fucα1-2)Galβ1-3Galβ1-4Galβ1-4Glc | GalNAcα1-3(Fucα1-2)Galβ1-3(4)GlcNAcβ1-3Galβ1-4Glc |
| 55 | GalNAcα1-3(Fucα1-2)Galβ1-4GlcNAcβ1-3Galβ1-4GlcNAcβ1-3Galβ1-4Galβ1-4Glc | GalNAcα1-3(Fucα1-2)Galβ1-4Galβ1-3(Galβ1-6)Galβ1-4Glc |
| 56 | GalNAcα1-3(Fucα1-2)Galβ1-4Galβ1-3(GalNAcα1-3Galβ1-6)Galβ1-4Glc | GalNAcα1-3(Fucα1-2)Galβ1-3(GalNAcα1-3Galβ1-6)Galβ1-4Glc |
| 57 | GalNAcα1-3(Fucα1-2)Galβ1-4Galβ1-3(GlcNAcα1-4Galβ1-6)Galβ1-4Glc | Galβ1-4(Fucα1-3)GlcNAcβ1-4Galβ1-3Galβ1-4Glc |
| 58 | GalNAcα1-3(Fucα1-2)Galβ1-4GlcNAcβ1-3(GlcNAcβ1-4GlcNAcβ1-6)Galβ1-4GlcNAcβ1-4GlcNAcβ1-3(GlcNAcβ1-6)Galβ1-4Glc | GalNAcα1-3(Fucα1-2)Galβ1-4GlcNAcβ1-3(GlcNAcβ1-4GlcNAcβ1-4)(GalNAcα1-3(Fucα1-2)Galβ1-4GlcNAcβ1-6)Galβ1-4GlcNAcβ1-4GlcNAcβ1-3(GlcNAcβ1-4Galβ1-4GlcNAcβ1-3)Galβ1-4Glc |
| 59 | GalNAcα1-3(Fucα1-2)Galβ1-3(4)GlcNAcβ1-3(Fucα1-2Galβ1-3(4)GlcNAcβ1-6)Galβ1-4GlcNAcβ1-3(Galβ1-4GlcNAcβ1-3(Galβ1-4GlcNAcβ1-6)Galβ1-4GlcNAcβ1-6)Galβ1-4Galβ1-4Glc | NeuAcα2-3Gal |
| 60 | NeuGcα2-3Gal | NeuAcα2-3Galβ1-4Glc |
| 61 | NeuGcα2-3Galβ1-4Glc | NeuNH2α2-3Galβ1-4Glc |
| 62 | Ac—O-4NeuGcα2-3Galβ1-4Glc | NeuAcα2-8NeuAcα2-3Galβ1-4Glc |
| 63 | NeuGcα2-8NeuAcα2-3Galβ1-4Glc | NeuAcα2-8NeuGcα2-3Galβ1-4Glc |
| 64 | NeuGcα2-8NeuGcα2-3Galβ1-4Glc | Ac—O-9NeuAcα2-8NeuAcα2-3Galβ1-4Glc |

TABLE 4

| | | |
|---|---|---|
| 65 | NeuAcα2-8NeuAcα2-8Neuα2-3Galβ1-4Glc | Ac—O-9NeuAcα2-8NeuAcα2-8NeuAcα2-3Galβ1-4Glc |
| 66 | GalNAcβ1-4(NeuAcα2-3)Galβ1-4Glc | GalNAcβ1-4(NeuGcα2-3)Galβ1-4Glc |
| 67 | Galβ1-3GalNAcβ1-4(NeuAcα2-3)Galβ1-4Glc | Galβ1-3GalNAcβ1-4(NeuGcα2-3)Galβ1-4Glc |
| 68 | Fucα1-2Galβ1-3GalNAcβ1-4(NeuAcα2-3)Galβ1-4Glc | Fucα1-2Galβ1-3GalNAcβ1-4(NeuGcα2-3)Galβ1-4Glc |
| 69 | Fucα1-3Galβ1-3GalNAcβ1-4(NeuAcα2-3)Galβ1-4Glc | Galα1-3Galβ1-3GalNAcβ1-4(NeuAcα2-3)Galβ1-4Glc |
| 70 | GalNAcβ1-4Galβ1-3GalNAcβ1-4(NeuAcα2-3)Galβ1-4Glc | GalNAcα1-3GalNAcβ1-3Galβ1-3GalNAcβ1-4(NeuAcα2-3)Galβ1-4Glc |
| 71 | Galβ1-3(Fucα1-2)Galβ1-3GalNAcβ1-4(NeuAcα2-3)Galβ1-4Glc | Galβ1-3Galα1-3Galβ1-3GalNAcβ1-4(NeuAcα2-3)Galβ1-4Glc |
| 72 | Galα1-3Galβ1-3Galα1-3Galβ1-3GalNAcβ1-4(NeuAcα2-3)Galβ1-4Glc | NeuAcα2-3Galβ1-3GalNAcβ1-4(NeuAcα2-3)Galβ1-4Glc |
| 73 | NeuAc(NeuGc)α2-3Galβ1-3GalNAcβ1-4(NeuGc(NeuAc)α2-3)Galβ1-4Glc | NeuGcα2-3Galβ1-3GalNAcβ1-4NeuGcα2-3Galβ1-4Glc |
| 74 | NeuAc9—O—Acα2-3Galβ1-3GalNAcβ1-4(NeuAcα2-3)Galβ1-4Glc | GalNAcβ1-4(NeuAcα2-3)Galβ1-3GalNAcβ1-4(NeuAcα2-3)Galβ1-4Glc |
| 75 | NeuAcα2-8NeuAcα2-3Galβ1-3GalNAcβ1-4(NeuAcα2-3)Galβ1-4Glc | GalNAcβ1-4(NeuAcα2-8NeuAcα2-3)Galβ1-4Glc |
| 76 | Galβ1-3GalNAcβ1-4(NeuAcα2-8NeuAcα2-3)Galβ1-4Glc | Fucα1-2Galβ1-3GalNAcβ1-4(NeuAcα2-8NeuAcα2-3)Galβ1-4Glc |
| 77 | Galα1-3Galβ1-3GalNAcβ1-4(NeuAcα2-8NeuAcα2-3)Galβ1-4Glc | Galα1-3Galα1-3Galβ1-3GalNAcβ1-4(NeuAcα2-8NeuAcα2-3)Galβ1-4Glc |
| 78 | Galα1-3(Fucα1-2)Galβ1-3GalNAcβ1-4(NeuAcα2-8NeuAcα2-3)Galβ1-4Glc | NeuAcα2-3Galβ1-3GalNAcβ1-4(NeuAcα2-8NeuAcα2-3)Galβ1-4Glc |
| 79 | NeuAcα2-3Galβ1-3GalNAcβ1-4(NeuAc9—O—Acα2-8NeuAcα2-3)Galβ1-4Glc | NeuAcα2-8NeuAcα2-3Galβ1-3GalNAcβ1-4(NeuAcα2-8NeuAcα2-3)Galβ1-4Glc |

TABLE 4-continued

| | | |
|---|---|---|
| 80 | GalNAcβ1-4(NeuAcα2-8NeuAcα2-8NeuAcα2-3)Galβ1-4Glc | Galβ1-3GalNAcβ1-4(NeuAcα2-8NeuAcα2-8NeuAcα2-3)Galβ1-4Glc |
| 81 | NeuAcα2-3Galβ1-3GalNAcβ1-4(NeuAcα2-8NeuAcα2-8NeuAcα2-3)Galβ1-4Glc | NeuAcα2-8NeuAcα2-3Galβ1-3GalNAcβ1-4(NeuAcα2-8NeuAcα2-8NeuAcα2-3)Galβ1-4Glc |
| 82 | NeuAcα2-3Galβ1-3GalNAcβ1-4Galβ1-4Glc | NeuGcα2-3Galβ1-3GalNAcβ1-4Galβ1-4Glc |
| 83 | GalNAcβ1-4(NeuAcα2-3)Galβ1-3GalNAcβ1-4Galβ1-4Glc | GalNAcβ1-4(NeuGcα2-3)Galβ1-3GalNAcβ1-4Galβ1-4Glc |
| 84 | Galβ1-3GalNAcβ1-4(NeuGcα2-3)Galβ1-3GalNAcβ1-4Galβ1-4Glc | Galβ1-3(NeuAcα2-6)GalNAcβ1-4Galβ1-4Glc |

TABLE 5

| | | |
|---|---|---|
| 85 | NeuAcα2-3Galβ1-3(NeuAcα2-6)GalNAcβ1-4Galβ1-4Glc | NeuAcα2-3Galβ1-3(NeuAcα2-8NeuAcα2-6)GalNAcβ1-4Galβ1-4Glc |
| 86 | NeuAcα2-8NeuAcα2-3Galβ1-3(NeuAcα2-6)GalNAcβ1-4Galβ1-4Glc | NeuAcα2-8NeuAcα2-3Galβ1-3(NeuAcα2-8NeuAcα2-6)GalNAcβ1-4Galβ1-4Glc |
| 87 | NeuAcα2-3Galβ1-3(NeuAcα2-6)GalNAcβ1-4(NeuAcα2-3)Galβ1-4Glc | NeuAcα2-3Galβ1-3GalNAcβ1-3Galα1-4Galβ1-4Glc |
| 88 | NeuGcα2-3Galβ1-3GalNAcβ1-3Galα1-4Galβ1-4Glc | NeuAcα2-8NeuAcα2-3Galβ1-3GalNAcβ1-3Galα1-4Galβ1-4Glc |
| 89 | NeuGcα2-8NeuGcα2-3Galβ1-3GalNAcβ1-3Galα1-4Galβ1-4Glc | NeuAcα2-3Galβ1-3(NeuAcα2-6)GalNAcβ1-3Galα1-4Galβ1-4Glc |
| 90 | NeuAcα2-3Galβ1-3GalNAcβ1-3Galα1-3Galβ1-4Glc | NeuAcα2-3Galβ1-3GlcNAcβ1-3Galβ1-4Glc |
| 91 | NeuAcα2-3Galβ1-3(Fucα1-4)GlcNAcβ1-3Galβ1-4Glc | GalNAcβ1-4(NeuAcα2-3)Galβ1-3GlcNAcβ1-3Galβ1-4Glc |
| 92 | NeuAcα2-3Galβ1-3Galβ1-3GlcNAcβ1-3Galβ1-4Glc | NeuAcα2-3Galβ1-3(NeuAcα2-6)GlcNAcβ1-3Galβ1-4Glc |
| 93 | NeuAcα2-3Galβ1-3(Fucα1-4))(NeuAcα2-6)GlcNAcβ1-3Galβ1-4Glc | NeuAcα2-3Galβ1-4GlcNAcβ1-3Galβ1-4Glc |
| 94 | NeuAcα2-3Galβ1-3GlcNAcβ1-3Galβ1-4Glc | NeuAcα2-6Galβ1-4GlcNAcβ1-3Galβ1-4Glc |
| 95 | NeuAcα2-8NeuAcα2-3Galβ1-4GlcNAcβ1-3Galβ1-4Glc | NeuGcα2-8NeuGcα2-3Galβ1-4GlcNAcβ1-3Galβ1-4Glc |
| 96 | NeuAcα2-8NeuGcα2-3Galβ1-4GlcNAcβ1-3Galβ1-4Glc | NeuAcα2-8NeuAcα2-8NeuAcα2-3Galβ1-4GlcNAcβ1-3Galβ1-4Glc |
| 97 | GalNAcβ1-4(NeuAcα2-3)Galβ1-4GlcNAcβ1-3Galβ1-4Glc | NeuAcα2-3Galβ1-4(Fucα1-3)GlcNAcβ1-3Galβ1-4Glc |
| 98 | NeuAcα2-6Galβ1-4GlcNAcβ1-3(Galβ1-4GlcNAcβ1-6)Galβ1-4Glc | NeuAcα2-3Galβ1-4GlcNAcβ1-3Galβ1-4GlcNAcβ1-3Galβ1-4Glc |
| 99 | NeuGcα2-3Galβ1-4GlcNAcβ1-3Galβ1-4GlcNAcβ1-3Galβ1-4Glc | NeuAcα2-6Galβ1-4GlcNAcβ1-3Galβ1-4GlcNAcβ1-3Galβ1-4Glc |
| 100 | NeuAcα2-3Galβ1-4GlcNAcβ1-(3Galβ1-4GlcNAcβ1)2-3Galβ1-4Glc | NeuAcα2-3Galβ1-4GlcNAcβ1-3Galβ1-4(Fucα1-3)GlcNAcβ1-3Galβ1-4Glc |
| 101 | NeuAcα2-3Galβ1-4GlcNAcβ1-3Galβ1-4(Fucα1-3)GlcNAcβ1-3Galβ1-4GlcNAcβ1-3Galβ1-4Glc | NeuAcα2-3Galβ1-4GlcNAcβ1-3Galβ1-4(Fucα1-3)GlcNAcβ1-(3Galβ1-4GlcNAcβ1)2-3Galβ1-4Glc |
| 102 | NeuAcα2-3Galβ1-3GalNAcα1-3(Fucα1-2)Galβ1-4GlcNAcβ1-3Galβ1-4Glc | NeuAcα2-3Galβ1-4GlNAcα1-3(Galβ1-4GlcNAcβ1-6)Galβ1-4GlcNAcβ1-3Galβ1-4Glc |
| 103 | NeuAcα2-3Galβ1-4GlcNAcα1-3(Fucα1-2Galβ1-4GlcNAcβ1-6)Galβ1-4GlcNAcβ1-3Galβ1-4Glc | NeuAcα2-3Galβ1-4GlcNAcα1-3(NeuAcα2-3Galβ1-4GlcNAcβ1-6)Galβ1-4GlcNAcβ1-3Galβ1-4Glc |

TABLE 6

| | | |
|---|---|---|
| 104 | NeuAcα2-3Galβ1-4GlcNAcβ1-3Galβ1-4GlcNAcβ1-3(6)(NeuAcα2-3Galβ1-4GlcNAcβ1-3(6))Galβ1-4GlcNAcβ1-3Galβ1-4Glc | NeuAcα2-3Galβ1-4GlcNAcβ1-3(NeuAcα2-3Galβ1-4GlcNAcβ1-6)Galβ1-4GlcNAcβ1-3(6)(NeuAcα2-3Galβ1-4GlcNAcβ1-3(6))Galβ1-4GlNAcβ1-3Galβ1-4Glc |
| 105 | NeuAcα2-3Galβ1-4GlcNAcβ1-3(Galα1-3Galβ1-4GlcNAcβ1-6)Galβ1-4GlcNAcβ1-3Galβ1-4Glc | NeuAcα2-3Galβ1-4GlcNAcβ1-3(GalNAcβ1-4)Galβ1-4Glc |
| 106 | GalNAcβ1-4(NeuAcα2-3)Galβ1-4GlcNAcβ1-3(GalNAcβ1-4)Galβ1-4Glc | NeuAcα2-3Galβ1-3GalNAcβ1-4Glc |
| 107 | GalNAcα1-3(Fucα1-2)Galβ1-3GalNAcβ1-3Galα1-4Galβ1-4Glc | Galα1-3(Fucα1-2)Galβ1-3GalNAcβ1-3Galα1-4Galβ1-4Glc |
| 108 | Neu5Acα2-3Galβ1-3GalNAcβ1-3Gal | GalNAcα1-3GalNAcβ1-3Galα1-4Galβ1-4Glc | wherein, the sugar chain is immobilized on the base material.

[2] The sugar chain array described in [1], wherein the base material is coated with a polymeric compound containing a unit having a primary amino group, and a sugar chain is immobilized on the base material by bonding the primary amino group to a reducing group on the end of the sugar chain.

[3] The sugar chain array described in [2], wherein the polymeric compound further contains a unit for maintaining hydrophilicity and a unit having a hydrophobic group.

[4] The sugar chain array described in [3], wherein the polymeric compound is represented by the following general formula [1]:

[1]

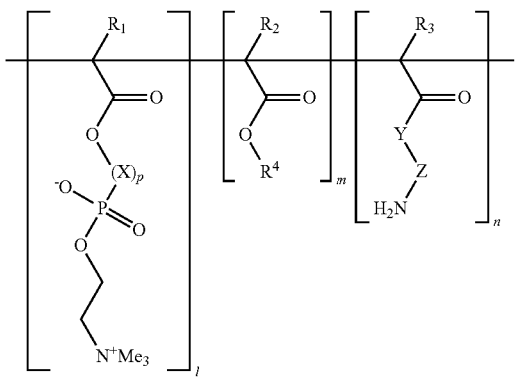

(wherein, R1, R2 and R3 represent hydrogen atoms or methyl groups, R4 represents a hydrophobic group, X represents an alkyleneoxy group having 1 to 10 carbon atoms, p represents an integer of 1 to 20 and in the case p is an integer of 2 to 20, the repeating X may be the same or different, Y represents a spacer containing an alkylene glycol residue, Z represents an oxygen atom or NH, and l, m and n represent natural numbers).

[5] The sugar chain array described in [4], wherein, in the polymeric compound represented by general formula [1], Y is represented by the following general formula [2] or general formula [3]:

[2]

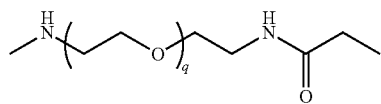

(wherein, q and r represent integers of 1 to 20)

[3]

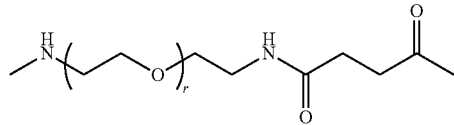

(wherein, q and r represent integers of 1 to 20).

[6] The sugar chain array described in any of [2] to [5], wherein the primary amino group in the polymeric compound is an oxylamino group and/or hydrazide group.

[7] The sugar chain array described in [6], wherein the content of the unit having a primary amino group in the polymeric compound is 20 mol % to 40 mol % of all units of the polymeric compound.

[8] The sugar chain array described in [4], wherein X represents an ethyleneoxy group in general formula [1].

[9] The sugar chain array described in any of [2] to [8], wherein the main chain of the polymeric compound is a (meth)acrylic backbone.

[10] The sugar chain array described in [4], wherein the hydrophobic group R4 in general formula [1] is an alkyl group having 2 to 10 carbon atoms.

[11] The sugar chain array described in [10], wherein the hydrophobic group R4 in general formula [1] is a cyclic alkyl group.

[12] The sugar chain array described in [11], wherein the cyclic alkyl group is a cyclohexyl group.

Effects of the Invention

Use of the sugar chain array of the present invention makes it possible to efficiently detect interaction between an analyte and a sugar chain. In particular, in this sugar chain array, by using a base material coated with a polymeric compound containing a unit having a primary amino group, a unit for maintaining hydrophilicity, and a unit having a hydrophobic group, the sugar chain can be immobilized efficiently and non-specific adsorption and binding of the analyte can be inhibited.

BEST MODE FOR CARRYING OUT THE INVENTION

The present invention provides a sugar chain array having at least one sugar chain selected from the group composed of sugar chains described in the aforementioned Tables 1 to 6 immobilized on a base material. The sugar chain array of the present invention can be used to detect binding between a sugar chain and an analyte (desired substance for detecting binding with, for example, a protein such as lecthin, a pathogen of a specific infectious disease and a secretion thereof, or other sugar chain). For example, since sugar chains among the sugar chains described in the aforementioned Tables 1 to 6 that contain sialic acid on a non-reducing terminal are recognized by influenza virus, an array having these sugar chains immobilized thereon is useful for diagnosing infection by influenza virus or developing a therapeutic drug against influenza virus. In addition, since sugar chains among the sugar chains described in the aforementioned Tables 1 to 6 that have N-acetyllactosamine and a repeating structure thereof bind with galectin, which has been suggested to be related to diseases such as cancer, an array having these sugar chains immobilized thereon is useful for diagnosing diseases such as cancer or developing a therapeutic drug against diseases such as cancer. The sugar chain array of the present invention preferably has two or more of the sugar chains selected from the group consisting of the sugar chains described in the aforementioned Tables 1 to 6 immobilized thereon (and for example, 5 or more, 10 or more, 30 or more, 50 or more, 100 or more, 150 or more or 200 or more).

The base material in the sugar chain array of the present invention is preferably coated with a polymeric compound containing a unit having a primary amino group. A sugar chain can be immobilized on the base material by bonding the primary amino group in the base material to a reducing terminal of the sugar chain.

The polymeric compound in the base material preferably further contains a unit for maintaining hydrophilicity and a unit having a hydrophobic group. In this form of base material, the unit for maintaining hydrophilicity fulfills the role of inhibiting physical adsorption (non-specific adsorption) of an analyte to the base material, while the unit having a hydrophobic group fulfills the role of binding the polymeric compound to the base material.

The hydrophilic unit contained in the polymeric compound is typically represented by a phosphorylcholine group, and although there are no particular limitations on the structure thereof, the unit represented by the following general formula [1] most preferably has a structure in which a (meth)acrylic residue and a phosphorylcholine group are bound through a chain of alkylene oxide groups X having 1 to 10 carbon atoms as indicated by the left structural unit of the structural units. In particular, X is most preferably an ethylene oxide group. The number of repeating alkylene oxide groups in the formula is an integer of 1 to 20, and in the case the number of repeating units is 2 to 20, the number of carbon atoms of the repeating alkylene oxide groups may be the same or different. Although 1 is inherently a natural number, it may be represented as a component ratio of each constituent unit.

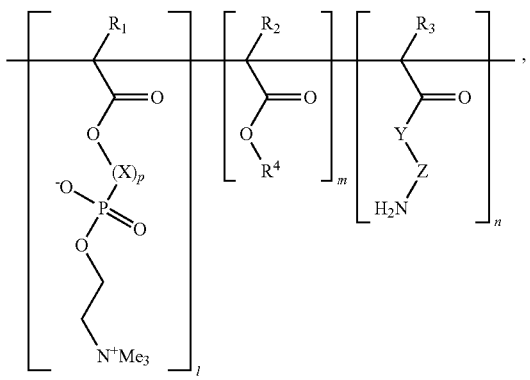

The component ratio of a unit having a phosphorylcholine group contained in the polymeric compound (ratio of l to the sum of l, m and n) is preferably 5 mol % to 98 mol %, more preferably 10 mol % to 80 mol %, and most preferably 10% to 80% of all units of the polymeric compound. If the component ratio is below the lower limit value, hydrophilicity diminishes and non-specific adsorption increases. On the other hand, if the component ratio exceeds the upper limit value, water solubility increases resulting in the possibility of the polymeric compound eluting during an assay.

Although there are no particular limitations on the unit having a hydrophobic group contained in the polymeric compound of the present invention, the structure is preferably that in which a hydrophobic group is bound to a (meth)acrylic group residue as is represented by the middle structural unit of the structural units shown in the aforementioned general formula [1]. Although there are no particular limitations thereon, examples of the hydrophobic group include alkyl groups and aromatics. The hydrophobic group is more preferably an alkyl group in which the alkyl moiety has 2 to 10 carbon atoms. There are no particular limitations on the structure of the alkyl group, and may be linear, branched or cyclic. As a result of a unit having a hydrophobic group being contained in the polymeric compound, wetting with respect to plastic and other hydrophobic base materials is improved, thereby enabling even coating. In addition, since hydrophobicity increases, the polymeric compound can be prevented from eluting during an assay. In the formula, although m is inherently a natural number, it may be represented as the component ratio of each constituent.

The component ratio of the unit having a hydrophobic group contained in the polymeric compound (ratio of m to the sum of l, m and n) is preferably 10 mol % to 90 mol %, more preferably 10 mol % to 80 mol %, and most preferably 20% to 80% of all units of the polymeric compound. If the component ratio exceeds the upper limit value, there is the risk of an increase in non-specific adsorption.

Although there are no particular limitations on the structure of the unit having a primary amino group contained in the polymeric compound of the present invention, the structure is preferably that connected through a spacer Y containing a (meth)acrylic residue and an oxylamino residue. Z represents an oxygen atom in the case of an oxylamino group, while Z represents NH in the case of a hydrazide group. Although n is inherently a natural number, it may also be indicated as the component ratio of each component. Although there are no particular limitations on the structure of the spacer Y containing an alkylene glycol residue, the structure thereof is preferably represented by the following general formula [2] or general formula [3], and is more preferably represented by general formula [2].

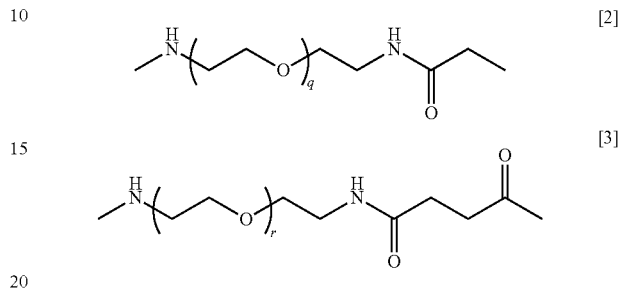

The component ratio of the unit having a primary amino group contained in the polymeric compound of the present invention (ratio of n to the sum of l, m and n) is preferably 1 mol % to 94 mol %, more preferably 2 mol % to 90 mol %, and most preferably 20% to 40% of all units of the polymeric compound. If the component ratio is below the lower limit value, the sugar chain can no longer be immobilized in an adequate amount. In addition, if the component ratio exceeds the upper limit value, non-specific adsorption increases.

Although there are no particular limitations on the method used to synthesize the polymeric compound of the present invention, from the viewpoint of ease of synthesis, the production method preferably at least comprises a step for radical copolymerizing a monomer having a phosphorylcholine group, a monomer having a hydrophobic group, and a monomer in which a primary amino group has been preliminarily protected with a protecting group, and a step for removing the protecting group from the polymeric compound obtained in that step. Alternatively, the production method preferably at least comprises a step for radical copolymerizing a monomer having a phosphorylcholine group, a monomer having a hydrophobic group, and a monomer having a functional group capable of introducing a primary amino group, and a step for introducing the primary amino group into the polymeric compound obtained in that step.

There are no particular limitations on the structure of the monomer having a phosphorylcholine group, and although examples include 2-(meth)acryloyloxyethylphosphorylcholine, 2-(meth)acryloyloxyethoxyethylphosphorylcholine, 6-(meth)acryloyoxyhexylphosphorylcholine, 10-(meth)acryloyloxyethoxynonylphosphorylcholine and 2-(meth)acryloyloxypropylphosphorylcholine; 2-methacryloyloxyethylphosphorylcholine is preferable from the viewpoint of availability.

Specific examples of monomers having a hydrophobic group include n-butyl(meth)acrylate, iso-butyl(meth)acrylate, sec-butyl(meth)acrylate, t-butyl(meth)acrylate, n-neopentyl(meth)acrylate, iso-neopentyl(meth)acrylate, sec-neopentyl(meth)acrylate, neopentyl(meth)acrylate, cyclohexyl (meth)acrylate, n-hexyl(meth)acrylate, iso-hexyl(meth)acrylate, heptyl(meth)acrylate, n-octyl(meth)acrylate, iso-octyl(meth)acrylate, 2-ethylhexyl(meth)acrylate, n-nonyl (meth)acrylate, iso-nonyl(meth)acrylate, n-decyl(meth) acrylate, iso-decyl(meth)acrylate, n-dodecyl(meth)acrylate, iso-dodecyl(meth)acrylate, n-tridecyl(meth)acrylate, iso-tridecyl(meth)acrylate, n-tetradecyl(meth)acrylate, iso-tetradecyl(meth)acrylate, n-pentadecyl(meth)acrylate, iso-pentadecyl(meth)acrylate, n-hexadecyl(meth)acrylate, isohexadecyl(meth)acrylate, n-octadecyl(meth)acrylate, isooctadecyl(meth)acrylate and isononyl(meth)acrylate. Among these, cyclohexyl(meth)acrylate, n-butylmethacrylate, n-dodecylmethacrylate and n-octylmethacrylate are most preferable.

Although there are no particular limitations on the structure of the monomer in which a primary amino group is preliminarily protected with a protecting group, the structure is preferably that in which a (meth)acrylic group and an oxylamino group or a hydrazide group are connected through a spacer Y containing an alkylene glycol residue as represented by the following general formula [4] (wherein, R3 represents a hydrogen atom or methyl group, Y represents a spacer containing an alkylene glycol residue, Z represents an oxygen atom or NH, and W represents a protecting group).

[4]

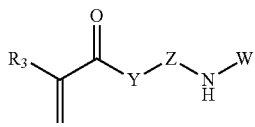

There are no restrictions on the protecting group W provided it is able to protect an amino group, and any arbitrary protecting group can be used. In particular, a t-butoxycarbonyl group (Boc group), benzyloxycarbonyl group (Z group, Cbz group) or 9-fluorenylmethoxycarbonyl group (Fmoc group) and the like are used preferably.

A specific example of this monomer is represented by the formula indicated below.

[5]

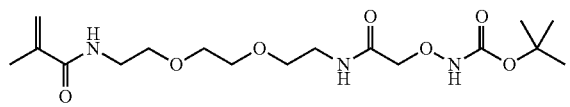

Deprotection can be carried out under ordinary conditions if trifluoroacetic acid, hydrochloric acid or anhydrous hydrofluoric acid is used.

On the other hand, although there are no restrictions on the method used to introduce a primary amino group after having polymerized the polymeric compound, the method is preferably a simple method that at least consists of radical copolymerizing a monomer having a phosphorylcholine group, a monomer having a hydrophobic group, and a monomer having an alkoxy group, followed by reacting the alkoxy group introduced into the polymeric compound with hydrazine to form a hydrazide group. Preferable examples of the alkoxy group include a methoxy group, ethoxy group, propoxy group and t-butoxy group.

A specific example of this monomer is represented by the formula indicated below.

[6]

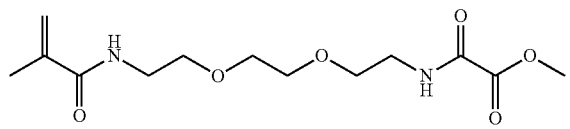

The synthesis solvent of the polymeric compound of the present invention may be any solvent in which each monomer dissolves, and examples thereof include alcohols such as methanol, ethanol, isopropanol, n-butanol, t-butyl alcohol or n-pentanol; and benzene, toluene, tetrahydrofuran, dioxane, dichloromethane, chloroform, cyclohexanone, N,N-dimethylformamide, dimethylsulfoxide, methyl acetate, ethyl acetate, butyl acetate, methyl ethyl ketone, methyl butyl ketone, ethylene glycol monoethyl ether, ethylene glycol monomethyl ether and ethylene glycol monobutyl ether. One type of these solvents may be used alone or two or more types may be used in combination.

An ordinary radical initiator may be used as polymerization initiator, and examples thereof include azo compounds such as 2,2'-azobisisobutyronitrile (to be referred to as "AIBN") or 1,1'-azobis(cyclohexane-1-carbonitrile), and organic peroxides such as benzoyl peroxide or lauryl peroxide.

The molecular weight of the polymeric compound of the present invention is such that the number average molecular weight is preferably 5000 or more and more preferably 10000 or more since this facilitates separation and purification of the polymeric compound and unreacted monomer.

Although deprotection can be carried out under ordinary conditions if the aforementioned trifluoroacetic acid, hydrochloric acid or anhydrous hydrofluoric acid is used, the time at which deprotection is carried out is as indicated below.

Normally, deprotection is carried out at the stage the polymeric compound can be produced following completion of polymerization, and the polymeric compound can be obtained by carrying out deprotection following completion of polymerization.

On the other hand, in the present invention, the property of inhibiting non-specific adsorption of a sugar chain and the property of immobilizing a sugar chain can be easily imparted by coating the polymeric compound onto the surface of a base material.

In this case, although a polymeric compound having a primary amino group that has been deprotected can also be coated, coating a polymeric compound having a highly reactive primary amino group after putting into solution may cause the primary amino group to react during the procedure and be deactivated depending on the particular case.

Thus, it is preferable to purify the polymeric compound and coat onto the surface of the base material immediately before deprotecting, followed by carrying out the deprotecting reaction to form a state in which the primary amino group is present on the surface of the base material.

Coating of the polymeric compound onto the surface of the base material is carried out by, for example, preparing a polymeric solution obtained by dissolving the polymeric compound in an organic solvent to a concentration of 0.05% by weight to 50% by weight, coating onto the surface of the base material using a known method such as immersion or spraying, and then drying either at room temperature or by heating.

Examples of organic solvents include alcohols such as methanol, ethanol, isopropanol, n-butanol, t-butyl alcohol, n-pentanol or cyclohexanol; and benzene, toluene, tetrahydrofuran, dioxane, dichloromethane, chloroform, aceton, methyl acetate, ethyl acetate, butyl acetate, methyl ethyl ketone, methyl butyl ketone, ethylene glycol monoethyl ether, ethylene glycol monomethyl ether, ethylene glycol monobutyl ether and cyclohexanone. One type of these solvents may be used alone or two or more types may be used in combination. Among these, alcohols such as ethanol, methanol, isopropanol, n-butanol, t-butyl alcohol, n-pentanol or cyclohexanol are preferable since they are dried easily without causing degeneration of plastic base materials.

A slide plate, 96-well plate, container or microfluidic plate is preferably used for the base material used in the present invention. Examples of these plates include a plastic plate, glass plate and plate having metallic film. Specific examples of plastic plates include plates made of materials such as polystyrene, cyclic polyolefin polymer, cycloolefin polymer, polypropylene, polyethylene, polysulfone, polyimide, polycarbonate or polymethyl methacrylate.

In particular, a plate made of cyclic polyolefin polymer or cycloolefin polymer is useful as a base material used to observe fluorescence. In the case of using the aforementioned base materials, if the hydrophobic group of the polymeric compound is a cyclohexyl group, interaction with the base material is favorable, and favorable results in terms of higher adsorbed amounts and lower background values are obtained in comparison with the case of coating a polymeric material of the same component ratio onto another base material (such as a polystyrene or glass base material).

In addition, in the case of coating the polymeric compound onto a cyclic poluolefin polymer, coating is not possible for a polymeric compound containing 100 mol % of an aminooxy monomer. On the other hand, although the polymeric compound can be coated onto a polystyrene polymer, this lacks versatility since non-specific adsorption of impurities is not inhibited.

Examples of methods used to immobilize sugar chains on the base material include a method consisting of spotting a solution in which a sugar chain or glycolipid (molecule in which a sugar chain is bound to a lipid) has been dissolved onto the base material using a spotter, and a method consisting of dispensing a solution in which a sugar chain or glycolipid has been dissolved into a container and the like and immobilizing thereon.

It is necessary to form a reducing sugar moiety on the terminal portion of the sugar chain in the molecule in order to immobilize the sugar chain on the surface of the aforementioned base material. Although there are no particular limitations on the oxidizing agent used, periodic acid can be used. The concentration thereof is 0.04 M to 0.16 M. In addition, a sodium bicarbonate solution (pH 8.1) is normally used for the buffer of this oxidation reaction. The sugar chain can be chemically immobilized by reacting an aldehyde group of a sugar chain oxidized in this manner with a primary amino group on a plate to form a Schiff base.

In addition, in the case of immobilizing a sugar chain on a base material when in the form of a glycolipid, the glycolipid can also be immobilized using the method described above by introducing a ketone group or aldehyde group into the lipid moiety instead of reducing the sugar chain and then using that group as a bonding point. Ozonolysis is an example of a method used to introduce a ketone group or aldehyde group into the glycolipid moiety.

More specifically, ozone gas is introduced by bubbling for 30 minutes through 200 μL of a chloroform-methanol (1:1 (v/v)) solution of a glycolipid having a concentration of 200 μM. Subsequently, the gas is replaced with nitrogen gas to remove the dissolved ozone. The ozonolysis reaction is stopped with 1 μL of triphenylphosphine (1 M toluene solution). After evaporating the reaction solution, hexane is added followed by stirring to obtain an ozonolysis product of the glycolipid (refer to reaction formula 1 indicated below).

[Reaction Formula 1]

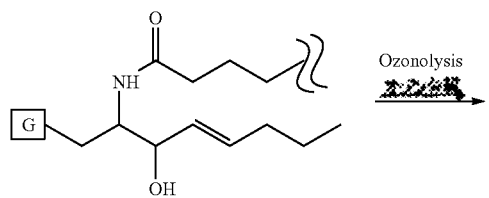

Ozonolysis

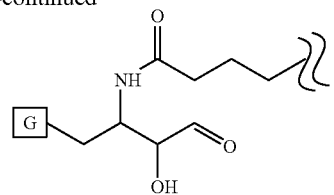

Various types of buffers are preferably used for the solution in which the sugar chain or glycolipid is dissolved. Although there are no particular limitations thereon, examples of buffers used include sodium carbonate, sodium hydrogen carbonate, potassium phosphate, dipotassium hydrogen phosphate, Tris-hydrochloride buffer, Tris-acetate buffer, PBS buffer, sodium citrate, sodium acetate, HEPES (N-2-hydroxyethylpiperazine-N'-ethanesulphonic acid) buffer and MOPS (3-(N-morpholino) propanesulfonic acid) buffer.

In the case of dissolving a sugar chain or glycolipid, the pH of the solution is preferably 2 to 8. Although there are no particular limitations on the concentration of the sugar chain or glycolipid in the solution, it is preferably 0.0001 mg/ml to 10 mg/ml. The temperature at which the solution of sugar chain or glycolipid is immobilized is preferably 0° C. to 100° C.

EXAMPLES

Although the following provides a more detailed explanation of the present invention based on an example and comparative example, the present invention is not limited to the following example.

Example

A cyclic polyolefin resin (hydrogenation product of a ring-opened polymer of 5-methyl-2-norbornene, MFR (melt flow rate): 21 g/10 min, hydrogenation rate: substantially 100%, thermal deformation temperature: 123° C.) was formed into the shape of a slide glass (dimensions: 75 mm×25 mm×1 mm) to fabricate a solid substrate. This solid substrate was immersed in a 0.3% by weight ethanol solution of a copolymer consisting of 2-methacryloyloxyethylphosphorylcholine (MPC), n-butylmethacrylate (BMA) and N-[2-[2-[2-(t-butoxycarbonyl-aminooxyacetylamino)ethoxy]ethoxy]ethyl]-methacrylamide (OA) (ratio of each group as mol %: 26:66:8) followed by drying to introduce a layer containing the aforementioned polymeric substance onto the substrate surface.

Comparative Example

The solid substrate of the example was used without coating with the polymeric substance.

(Immobilization of Glycolipid Sugar Chain)

Next, a solution prepared so that a sugar chain moiety of a ganglioside-based glycolipid was present at a concentration of 0.5 mM in 0.5 M acetate buffer was spotted onto the supports obtained in the example and comparative example using an automated spotter followed by immobilizing by allowing to stand undisturbed for 1 hour at 80° C. The supports were washed with ultrapure water following immobilization.

(Reaction with Sugar Chain-Binding Protein)

Next, a solution in which was dissolved a sugar chain-binding protein in the form of labeled cholera toxin B subunit (Molecular Probes Inc.) was contacted with the aforementioned washed supports at each of the concentrations shown in Table 8 (solvent: Tris buffer containing 0.05% by weight Tween 20), followed by carrying out a sugar chain-protein specific reaction by allowing to stand undisturbed for 2 hours at room temperature. Following the reaction, each support was washed for 2 minutes at room temperature using Tris buffer containing 0.05% by weight Triton X-100.

Fluorescence was measured for each of the spots on the supports as well as portions other than the spots (background) of the example and comparative example on which the aforementioned assay was carried out, followed by calculation of the difference between those values. The results are shown in Tables 7 and 8.

TABLE 7

At cholera toxin B subunit concentration of 2000 ng/mL

| Glycolipid Sugar Chain | Example | Comparative Example |
|---|---|---|
| GM1a | 746403 | 2038 |
| GM2 | 1044 | 339 |
| GM3 | 506 | 297 |
| GD1a | 37478 | 1116 |
| GD2 | 899 | 274 |
| GD3 | 444 | 198 |
| GT1a | 66362 | 1009 |
| GT2 | 1021 | 458 |
| GT3 | 345 | 96 |

(Values in table obtained by subtracting background value)

TABLE 8

| Cholera toxin subunit B concentration | Example | Comparative Example |
|---|---|---|
| 2000 ng/mL | 746403 | 2010 |
| 200 ng/mL | 422424 | 1527 |
| 20 ng/mL | 78530 | 304 |
| 2 ng/mL | 32192 | 150 |
| 0.2 ng/mL | 7647 | 22 |

A scanner manufactured by GE Healthcare Corp. (Typhoon TRIO+) was used to measure fluorescence levels for the example and comparative example. Measurement conditions consisted of PMT voltage of 600 V, excitation wavelength of 532 nm, measuring wavelength of 580 nm, and resolution of 25 μm.

In the case of the example, according to Table 7, only GM1a specifically bound with the cholera toxin B subunit, and according to Table 8, signals were able to be detected that were dependent on the concentration of the cholera toxin B subunit. On the other hand, in the case of the comparative example, there were no reactions at any of the sugar chain spots, and cholera toxin B subunit was unable to be detected. Namely, the glycolipid sugar chain chip of the present invention can be said to have been able to detect protein both specifically and concentration-dependently.

INDUSTRIAL APPLICABILITY

Use of the sugar chain array of the present invention makes it possible to efficiently detect an interaction between an analyte and a sugar chain. Since sugar chains are intimately involved in numerous vital phenomena and the pathologies of cancer, infectious diseases and the like, the sugar chain array of the present invention is able to greatly contribute to, for example, the development of new diagnostic and therapeutic methods.

The invention claimed is:

1. A sugar chain array, comprising: a base material comprising a cyclic polyolefin polymer; and at least one sugar chain selected from the group consisting of sugar chains from Tables 1, 2, 3, 4, 5 and 6:

{Table 1}
{Table 2}
{Table 3}
{Table 4}
{Table 5}
{Table 6};

wherein the sugar chain is immobilized on the base material, and the base material comprises a coating comprising a polymeric compound having formula [1]:

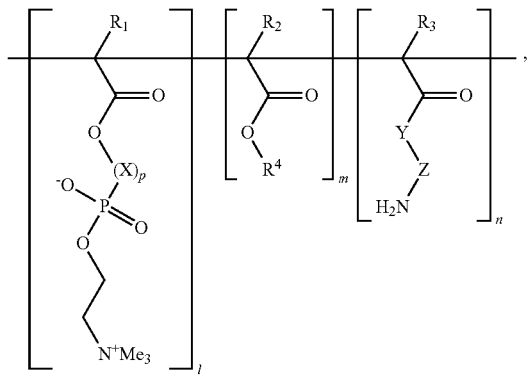

[1]

where R1, R2, and R3 are each independently a hydrogen atom or methyl group, R4 is a cyclohexyl group, X is an alkyleneoxy group comprising 1 to 10 carbon atoms, p is an integer from 1 to 20 and in the case that p is an integer of 2 to 20, the repeating X may be the same or different, Y is a spacer comprising an alkylene glycol residue, Z is an oxygen atom or NH, and l, m and n are each independently a natural number, wherein immobilization of the sugar chain occurs via Schiff base formation between the primary amine group of the polymeric compound and an aldehyde or ketone group of the sugar chain.

2. The sugar chain array of claim 1, wherein the sugar chain is immobilized on the base material by bonding the primary amino group of the polymeric compound to a reducing group on the end of the sugar chain.

3. The sugar chain array of claim 1, wherein, in formula [1], Y has formula [2]:

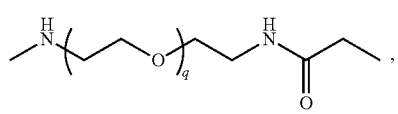

[2]

wherein, q is an integer from 1 to 20; or
Y has formula [3]:

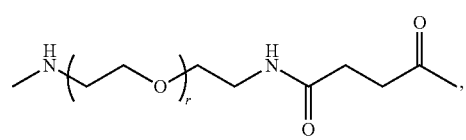

[3]

wherein r is an integer from 1 to 20.

4. The sugar chain array of claim 1, wherein the primary amino group in the polymeric compound is an oxylamino group.

5. The sugar chain array of claim 1, wherein the unit having the primary amino group in the polymeric compound is included in an amount of from 20 mol % to 40 mol % based on all units of the polymeric compound.

6. The sugar chain array of claim 1, wherein, in formula [1], X is an ethyleneoxy group.

7. The sugar chain array of claim 1, wherein the polymeric compound comprises a (meth)acrylic backbone.

8. The sugar chain array of claim 1, wherein the unit having a phosphorylcholine group in the polymeric compound is included in an amount of from 5 mol % to 98 mol % based on all units of the polymeric compound.

9. The sugar chain array of claim 1, wherein the unit having a phosphorylcholine group in the polymeric compound is included in an amount of from 10 mol % to 80 mol % based on all units of the polymeric compound.

10. The sugar chain array of claim 1, wherein the unit having R4 in the polymeric compound is included in an amount of from 10 mol % to 90 mol % based on all units of the polymeric compound.

11. The sugar chain array of claim 1, wherein the unit having R4 in the polymeric compound is included in an amount of from 10 mol % to 80 mol % based on all units of the polymeric compound.

12. The sugar chain array of claim 1, wherein the unit having R4 in the polymeric compound is included in an amount of from 20 mol % to 80 mol % based on all units of the polymeric compound.

13. The sugar chain array of claim 1, wherein the primary amino group in the polymeric compound is a hydrazide group.

* * * * *